United States Patent [19]
Gerde

[11] Patent Number: 6,003,512
[45] Date of Patent: Dec. 21, 1999

[54] DUST GUN-AEROSOL GENERATOR AND GENERATION

[75] Inventor: Per Magnus Gerde, Albuquerque, N. Mex.

[73] Assignee: Lovelace Respiratory Research Institute, Albuquerque, N. Mex.

[21] Appl. No.: 09/190,990

[22] Filed: Nov. 12, 1998

Related U.S. Application Data

[60] Provisional application No. 60/065,417, Nov. 13, 1997.

[51] Int. Cl.$^6$ .............................. A61M 15/00; B05B 7/32
[52] U.S. Cl. ................... 128/203.15; 222/636; 222/637; 239/8; 239/143; 239/337
[58] Field of Search ............................. 239/346, 67, 99, 239/325, 8, 143, 337, 654; 222/630, 636, 637; 128/200.14, 203.15, 203.21; 604/58

[56] References Cited

U.S. PATENT DOCUMENTS

| | | | |
|---|---|---|---|
| 3,785,568 | 1/1974 | Pfingsten et al. | 239/346 X |
| 4,017,007 | 4/1977 | Riccio | 222/80 |
| 4,184,258 | 1/1980 | Barrington et al. | 222/636 |
| 4,288,036 | 9/1981 | Jubinville | 239/346 X |
| 4,678,377 | 7/1987 | Bouchard | 222/630 X |
| 5,320,714 | 6/1994 | Brendel | 128/203.13 |
| 5,349,947 | 9/1994 | Newhouse et al. . | |
| 5,533,502 | 7/1996 | Piper . | |
| 5,558,085 | 9/1996 | Rubsamen et al. | 128/200.14 |
| 5,582,162 | 12/1996 | Petersson . | |
| 5,607,691 | 3/1997 | Hale et al. | 424/449 |
| 5,622,166 | 4/1997 | Eiscle . | |
| 5,669,378 | 9/1997 | Pera et al. | 128/203.21 |
| 5,687,710 | 11/1997 | Ambrosio et al. . | |
| 5,699,789 | 12/1997 | Hendricks . | |
| 5,724,959 | 3/1998 | McAughey et al. . | |
| 5,740,792 | 4/1998 | Ashley et al. . | |

FOREIGN PATENT DOCUMENTS

WO09/07351  7/1990  WIPO .

OTHER PUBLICATIONS

Adjei, A.L., et al., "Dry–Powder Inahalation Aerosols", *Inhalation Delivery of Therapeutic Peptides and Proteins*, ed. Adjei, A.L., et al., 625–665, Marcel Dekker, New York.

Arborelius, M., Jr., "Generation of a Microaerosol Suitable for Deposition in the Peripheral Airways", *Eur J Respir Dis Suppl 119*, 1982, 19–27, vol. 65.

Bohnet, M., "Calculation and Design of Gas/Solid–Injectors", *Powder Technology*, ed. K. Jinoya, et al., 1984, 302–313, Hemisphere Publishing Corporation.

Cheng, Y.–S., et al., "A Venturi Disperser As A Dry Powder Generator for Inhalation Studies", *Inhalation Toxicology*, 1989, 365–371, vol. 1.

Cheng, Y.–S., et al, "Use of a Jet Mill for Dispersing Dry Powder for Inhalation Studies", *Am. Ind. Hyg.Assoc. J.*, Aug., 1985, 449–454, vol. 46, Issue 8, American Industrial Hygiene Association.

Concessio, N.M., et al., "Impact Force Separation Measurements—Their Relevance in Powder Aerosol Formulation", *Respiratory Drug Delivery VI*, 1998, 251–258.

Coyne, T.C., "Introduction to the CFC Problem", *Journal of Aerosol Medicine*, 1991, 175–180, vol. 4, No. 3, Mary Ann Liebert, Inc.

Crompton, G.K., "Dry Powder Inhalers: Advantages and Limitations", *Journal of Aerosol Medicine*, 1991, 151–156, vol. 4, No. 3, Mary Ann Liebert, Inc. 2

(List continued on next page.)

*Primary Examiner*—Kevin Weldon
*Assistant Examiner*—Sean P. O'Hanlon
*Attorney, Agent, or Firm*—Nancy E. Ownbey; Deborah A. Peacock; Rod D. Baker

[57] ABSTRACT

An apparatus and method for aerosolizing and dispensing powders utilizing the forces of pressurizing and depressurizing gas loaded into powder agglomerates located in an enclosed powder chamber. Methods include administering peptides, genes, vitamins, and polymers into the peripheral lung. Also describes powder supply apparatus and method for single dose and repetitive applications.

78 Claims, 8 Drawing Sheets

OTHER PUBLICATIONS

Dolovich, M., "Physical Principles Underlying Aerosol Therapy", *Journal of Aerosol Medicine*, 1989, 171–186, vol. 2, No. 2, Mary Ann Liebert, Inc.

Drew, R.T., Ph.D., et al., "A New Dust–Generating System for Inhalation Studies", *American Industrial Hygiene Association Journal*, May, 1971, 327–330, vol. 32.

Ebens, R., et al., "A Device for the Continuous Metering of Small Dust Quantities", *Staub–Reinhalt. Luft*, May, 1968, 24–26, vol. 28, No. 5.

Eickelpasch, D., "Problems of Gravimetric Short–Time Dust Measurement", *Stabu–Reinhalt. Luft*, May, 1968, 25–26, vol. 28, No. 5.

Engel, T., "Patient–Related Side Effects of CFC Propellants", *Journal of Aerosol Medicine*, 1991, 163–167, vol. 4, No. 3, Mary Ann Liebert, Inc.

Fox, L.S., et al., "Performance of a venturi eductor as a feeder in a pneumatic conveying system", *Powder and Bulk Engineering*, Mar., 1988, 33–36.

Fuchs, Prof. Dr. N.A., et al., "Laboratory Powder Disperser (Dust Generator)", *Staub–Reinhalt. Lift*, Nov., 1970, 1–3, vol. 30, No. 11.

Gordieyeff, V.A. et al., Ph.D., "Studies on Dispersion of Solids as Dust Aerosols", *A.M.A. Arch. Ind. Health*, Jun., 1957, 510–515, vol. 15.

Gupta, P.K., "Key Worldwide Patents in Pulmonary Drug Delivery", *Inhalation Delivery of Therapeutic Peptides and Proteins*, ed. Adjei, A.L., et al., 1997, 817–860, Marcel Dekker, Inc., New York.

Hickey, A.J., "Factors Influencing the Dispersion of Dry Powders as Aerosols", *Pharmaceutical Technology*, Aug., 1994, 58–64.

Hinds, W.C., "Dry–Dispersion Aerosol Generators", *Generation of Aerosols and Facilities for Exposure Experiments*, ed. Willeke, K., 1979, 171–187, Ann Arbor Science, Ann Arbor, MI.

Hinds, W.C., "Production of Test Aerosols", *Aerosol Technology: Properties, Behavior, and Measurement of Airborne Particles*, 1982, 379–395, John Wiley & Sons.

Kim, C.S., et al., "Size Aspects of Metered–Dose Inhaler Aerosols", *Am Rev Respir Dis*, 1985, 137–142, vol. 132.

Lucas, P., et al., "The Role of Fine Particle Excipients in Pharmaceutical Dry Powder Aerosols", *Respiratory Drug Delivery VI*, 1998, 243–250.

Moren, F., "Drug Deposition of Pressurized Inhalation Aerosols", *Eur J Respir Dis Suppl 119*, 1982, 51–55, vol. 63.

Rubsamen, R., "Novel Aerosol Peptide Drug Delivery Systems", *Inhalation Delivery of Therapeutic Peptides and Proteins*, ed. Adjei, A.L., et al., 1997, 703–731, Marcel Dekker, Inc., New York.

Service, R.F., "Drug Delivery Takes a Deep Breath", *Science*, Aug. 29, 1997, 1199–1200, vol. 277.

Thompson, M.M., et al., "General Issues in Gene Delivery via the Lung", *Inhalation Delivery of Therapeutic Peptides and Proteins*, ed. Adjei, A.L., et al., 1997, 475–491, Marcel Dekker, Inc., New York.

Wright, B.M., "A New Dust–Feed Mechanism", *J Sci Instrum*, 1950, 12–15, vol. 27.

DUST GUN-AEROSOL GENERATOR AND GENERATION

CROSS-REFERENCE TO RELATED APPLICATIONS

This application is a continuation-in-part application of U.S. patent application Ser. No. 60/065,417, entitled Dust Gun, to Gerde, filed on Nov. 13, 1997, and the specification thereof is incorporated herein by reference.

GOVERNMENT RIGHTS

The U.S. Government has a paid-up license in this invention and the right in limited circumstances to require the patent owner to license others on reasonable terms as provided for by the terms of Contract No. 5 RO1 ES04422-09 awarded by U.S. Department of Health and Human Services, National Institutes of Health.

BACKGROUND OF THE INVENTION

1. Field of the Invention (Technical Field)

The present invention relates to aerosol generation, particularly for generating short bursts of finely divided particles from small portions of cohesive or non-cohesive powders by utilizing rapid decompression of powder particles, including agglomerated particles. Included in the invention are an apparatus and method of producing and using such aerosols.

2. Background Art

Aerosol generation systems are used in several different applications: In industry for injecting powders into tubes for pneumatic transport; in toxicology and industrial hygiene for generating study atmospheres; and in medicine for delivering particulate drugs to patients by the inhalation route. There are more design options available for continually working aerosol generators than for batch-wise devices. Several types of generators originally designed for continuous use include the following: the Venturi tube powder injector, which utilizes pressurized air (Bohnet M., Calculation and design of gas/solid injectors. *Powder Technology*, 302–313, 1984; Cheng, Y., Barr et al., "A Venturi dispenser as a dry powder generator for inhalation studies," *Inhalation Toxicology* 1: 365–371, 1989), the Wright dust feeder, which uses a rotating scraper, (Wright, B., "A new dust-feed mechanism", *Journal of Scientific Instruments*, 27: 12–15, 1950) and various fluidized bed designs, which use blowing air (Drew, R. and Laskin, S., "A new dust-generating system for inhalation studies", *American Industrial Hygiene Association Journal*, 32: 327–330, 1971; Ebens R. and Vos, M. "A device for the continuous metering of small dust quantities", *Staub-Reinhalt der Luft*, 28(5): 24–25, 1971).

For dispersion of dry powder medicaments there are three major methods of aerosolization available: Metered dose inhalers (MDI), passive dry powder inhalers (pDPI), and active dry powder inhalers (aDPI). MDIs use a volatile propellant (chlorofluorocarbons) under pressure to aerosolize the medicament. A small volume of the medicament suspended in the liquid propellant is ejected through a nozzle to ambient pressure. The flash boiling resulting from the rapid decompression of the propellant is the main mechanism of aerosolization. pDPIs use the energy of the patient's own breathing to fractionate the medicament into an inhalable aerosol. However, due to the nature of the energy source, it is difficult for some patients, for example with asthma, to achieve a sufficiently high peak respiratory flow rate to overcome agglomeration. This results in an increased deposition of the medicament in the oropharyngeal region. While spacers may alleviate this problem partially, they do not increase the total dose delivered to the lungs. The need for alternative technologies in this field has increased both because the Montreal Protocol will severely restrict the use of ozone-damaging chlorofluorocarbon propellants in MDIs after 1998 (Coyne, T. "Introduction to the CFC problem", *Journal of Aerosol Medicine* 4: 175–180. 1991), and because a multitude of new drugs, such as peptides, proteins and genes, are currently in development. Many of these potential drugs have been found to be particularly suitable for administration via the inhalation route (Rubsamen, R. "Novel aerosol peptide drug delivery systems", *Inhalation Delivery of Therapeutic Peptides and Proteins*, NY. 703–731, 1997; Thompson, M. and Weiner-Kronish, J. "General issues in gene delivery via the lung", *Inhalation Delivery of Therapeutic Peptides and Proteins*, NY., 475–491, 1997). Albeit many of these drugs have their therapeutic action within the airways or the peripheral lung, an increasing number of drugs are intended for distribution in the systemic circulation following absorption in the peripheral lung (alveoli). In the latter case, a high fractional delivery to the peripheral lung is necessary and can be accomplished if the delivery device can deliver the medicament in a particle size range of 1–5 $\mu$m at a low inspiratory flow rate (Service, R. "Drug delivery takes a deep breath", *Science* 277: 1199–1200, 1997). This need created the intense field of innovation in the area of active DPIs (Hickey, A., Concessio, N. et al. "Factors influencing the dispersion of dry powders as aerosols", *Pharmaceutical Technology* 58–64, 1994).

In active DPIs, the aerosol is either formed directly in a single step from the bulk powder, or in a two-step procedure where larger agglomerates are formed and further fractionated into an inhalable aerosol. Of aDPIs the Venturi tube is a commonly used design. The carrier gas flows through a smooth constriction followed by a gradually widening nozzle. The sonic shock at the constriction and the downstream turbulence are the major aerosolizing forces. The particles can be introduced with the gas stream, or sheared into the airstream at the flow constriction from a smaller particle feed conduit. Due to this design, however, particularly with more adhesive powders, is inevitable plugging of the tube at the flow constriction. Formulation of a less adhesive powder is an important and necessary part of using the Venturi tube design in a DPI. (Service, 1997). Because most other DPIs provide even less energy than Venturi tube designs to de-agglomerate particles, other means of rendering the powder suitable for dispersion and inhalation are used, such as mixing the powder with diluents or excipients. Diluents reduce intra-agglomeration forces, but add to the bulk and cost of the medication (Lucas, P., Clarke, M. et al. "The role of fine particle excipients in pharmaceutical dry powder aerosols", Respiratory Drug Delivery VI, S.C., "Drug deposition of pressurized inhalation aerosols", *European Journal of Respiratory Diseases*, 63 (Suppl 119): 51–55, 1998).

SUMMARY OF THE INVENTION (DISCLOSURE OF THE INVENTION)

The present invention is an apparatus for aerosolizing and dispensing powders. The apparatus comprises a pressure chamber, at least one ejecting conduit opening to ambient pressure, powder chamber, at least one pressure conduit connecting the pressure chamber and the powder chamber, and an exit nozzle.

In one embodiment, the ejecting conduit is a channel of substantially uniform cross-section. In another embodiment, the ejecting conduit is a cylinder.

In a preferred embodiment of the invention, the apparatus has a powder chamber comprising a base with an indentation for receiving powder. It may further comprise a lid, which comprises an indentation in one embodiment. The lid covers the base. The lid indentation is disposed over the base indentation. In a preferred embodiment, the powder chamber is a sphere.

The invention includes the exit nozzle and the ejecting conduit meeting at an angle at least 45° from an axial extension of the ejecting conduit and a plane of the exit nozzle. In one embodiment, the angle is at least 70°. In another embodiment, the angle is at least 90°.

One embodiment of the invention includes the powder chamber and ejecting conduit meeting at an angle greater than 60° from an axial extension from the ejecting conduit and a tangent of the powder chamber. In another embodiment, that angle is greater than 85°.

One embodiment of the present invention further comprises a fast-releasing valve. One embodiment of the present invention comprises a reservoir for holding powders. The apparatus further comprises a line connecting the reservoir and a powder chamber.

One embodiment of the present invention further comprises a pressurized gas supply. In another embodiment, the gas supply comprises nitrogen or one of the inert gases.

The invention includes an apparatus for aerosolizing and dispensing powders comprising a pressure chamber, a powder chamber, at least one pressure conduit connecting the pressure chamber and the powder chamber, an exit nozzle, and at least one ejecting conduit of substantially uniform cross-section. The ejecting conduit further comprises a cylinder in an alternative embodiment. Also in this apparatus is a powder chamber comprising a base with an indentation for receiving powder. It may further comprise a lid, which comprises an indentation in one embodiment. The lid covers the base. The lid indentation is disposed over the base indentation. In a preferred embodiment, the powder chamber is a sphere. This apparatus includes the exit nozzle and the ejecting conduit meeting at an angle at least 45° from an axial extension of the ejecting conduit and a plane of the exit nozzle. In one embodiment, the angle is at least 70°. In another embodiment, the angle is at least 90°. One embodiment of this apparatus includes the powder chamber and ejecting conduit meeting at an angle greater than 60° from an axial extension from the ejecting conduit and a tangent of the powder chamber. In another embodiment, that angle is greater than 85°. One embodiment of the present invention further comprises a fast-releasing valve. One embodiment of the present invention further comprises a pressurized gas supply.

The invention also includes an apparatus for aerosolizing and dispensing powders comprising a pressure chamber, at least one ejecting conduit, a powder chamber, the powder chamber and ejecting conduit meeting at an angle greater than 60° from an axial extension from the ejecting conduit and a tangent of the powder chamber, at least one pressure conduit connecting the powder chamber and the pressure chamber, and an exit nozzle. Alternatively, the angle in the apparatus is greater than 85°. The invention includes the exit nozzle and the ejecting conduit meeting at an angle at least 45° from an axial extension of the ejecting conduit and a plane of the exit nozzle. In one embodiment, the angle is at least 70°. In another embodiment, the angle is at least 90°. In an alternative embodiment, the ejecting conduit comprises a channel of substantially uniform cross-section. In another embodiment, the ejecting conduit comprises a cylinder. Also in this apparatus is a powder chamber comprising a base with an indentation for receiving powder. It may further comprise a lid, which comprises an indentation in one embodiment. The lid covers the base. The lid indentation is disposed over the base indentation. One embodiment of the present invention further comprises a fast-releasing valve. One embodiment of the present invention comprises a reservoir for holding powders. The apparatus further comprises a line connecting the reservoir and a powder chamber. One embodiment of the present invention further comprises a pressurized gas supply. In another embodiment, the gas supply comprises nitrogen or one of the inert gases.

The invention also includes an apparatus for aerosolizing and dispensing powders comprising a pressure chamber, at least one ejecting conduit, a powder chamber, at least one pressure conduit connecting the powder chamber and the pressure chamber, and an exit nozzle, where the exit nozzle and the ejecting conduit meet at an angle at least 45° from an axial extension of the ejecting conduit and a plane of the exit nozzle. In an alternative embodiment, the angle is at least 70°. In another embodiment, the angle is at least 90°. In one embodiment, the ejecting conduit comprises a channel of substantially uniform cross-section. In another embodiment, the ejecting conduit comprises a cylinder. Also in this apparatus is a powder chamber comprising a base with an indentation for receiving powder. It may further comprise a lid, which comprises an indentation in one embodiment. The lid covers the base. The lid indentation is disposed over the base indentation. In a preferred embodiment, the powder chamber is a sphere. One embodiment of this apparatus includes the powder chamber and ejecting conduit meeting at an angle greater than 60° from an axial extension from the ejecting conduit and a tangent of the powder chamber. In another embodiment, that angle is greater than 85°. One embodiment of the present invention further comprises a fast-releasing valve. One embodiment of the present invention further comprises a pressurized gas supply.

The invention is also a method of generating a fine aerosol from a powder substance comprising the steps of agitating with a pressurized gas a powder substance to create a suspension, ejecting the suspension through a narrow ejecting conduit, passing the pressurized suspension from the narrow conduit directly into an exit nozzle of sudden diameter increase into ambient pressure, and depressurizing the suspension to de-agglomerate the suspension. The invention further includes a method further comprising administering the suspension to a patient's lung. The method also includes the suspension reaching alveoli and peripheral lung. In one alternative of the invention, the method includes administering peptides, genes, vitamins, polymers or medicaments. One alternative of the present method comprises the step of ejecting the suspension through a narrow ejection conduit from the powder chamber where the powder chamber and the ejecting conduit meeting at an angle greater than 60° from an axial extension from the ejecting conduit and a tangent of the powder chamber. In another alternative embodiment, the angle is greater than 85°. In another embodiment, the method includes the step of passing the suspension through the ejection conduit directly into the exit nozzle where the exit nozzle and the ejecting conduit meet at an angle of at least 45° from an axial extension of the ejecting conduit and a plane of the exit nozzle. In yet another embodiment, the angle is at least 70°, and in a third embodiment, the angle is at least 90°.

One embodiment of the present invention further comprises a fast-releasing valve. One embodiment of the present invention further comprises a pressurized gas supply.

The invention also includes a method of generating a fine aerosol from an agglomerated powder wherein clogging of the aerosol generator is avoided comprising the steps of agitating with a pressurized gas an agglomerated powder to create a suspension in the aerosol generator, ejecting the suspension through a narrow ejecting conduit in the aerosol generator, passing the pressurized suspension from the narrow conduit directly into an exit nozzle of sudden diameter increase into ambient pressure, and depressurizing the suspension to de-agglomerate the suspension. The method further includes administering the suspension to a patient's lung, and further comprises administering the suspension to the peripheral lung. The suspension administered include peptides, genes, vitamins, polymers, and medicaments. One method uses the step of ejecting through an ejecting conduit of substantially uniform cross-section. Another method uses an ejecting conduit that is a cylinder.

The invention also includes a method of generating a fine aerosol from a powder comprising the steps of agitating with a pressurized gas a powder to create a suspension, ejecting the suspension through a narrow ejecting conduit of substantially uniform cross-section, passing the pressurized suspension from the narrow conduit directly into an exit nozzle of sudden diameter increase into ambient pressure, and depressurizing the suspension to de-agglomerate the suspension. This method further comprises the step of administering the suspension to a patient's lung. The method further comprises administering a suspension from the group of peptides, genes, vitamins, polymers, and medicaments. The method further comprises ejecting the suspension through an ejecting conduit wherein the ejecting conduit is a cylinder.

A primary object of the present invention is to provide an apparatus and method capable of producing a fine aerosol from a bulk powder or other substance for inhalation therapies or experiments.

Another object of the present invention is to provide an apparatus and method for producing aerosols capable of reaching the peripheral lung and tissues.

Another object of the present invention is to provide an apparatus and method for producing an aerosol to reach the peripheral lung without the use of chlorofluorocarbons.

Another object of the present invention is to provide an apparatus and method for producing a fine aerosol as an active dry powder inhaler without relying on the use of mechanical shear forces for creating desired particle size.

A primary advantage of the present invention is the lack of plugging or clogging of the apparatus during repeated use.

Another advantage of the present invention is the ability to create aerosols from "sticky" powders without the use of diluents or excipients.

Another advantage of the present invention is the smaller and more controlled volume ejected immediately at the exit nozzle of the apparatus.

Another advantage of the present invention is the ability to deliver the dose of the aerosolized powder into the peripheral lung and alveoli.

Other objects, advantages and novel features, and further scope of applicability of the present invention will be set forth in part in the detailed description to follow, in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

(BEST MODES FOR CARRYING OUT THE INVENTION)

The present invention provides a method and an apparatus to effectively aerosolize small batches of cohesive or non-cohesive powders to micron-sized aerosols by converting energy stored in pressurized gas into power for fractionating a powder. As used throughout the specification and claims, the term "aerosol" means any product of ejection of a powder. The energy stored in a pressurized gas is efficiently used to break up agglomerates of powder and eject a plume of fine particles at comparatively low air speeds. As used throughout the specification and claims, the term "agglomerates" means aggregates, agglomerates or particles held by any binding force, e.g. chemical or physical binding. As used throughout the specification and claims, the term "plane" means a tangent.

The present invention has a unique means of aerosol formation. Pressurized gas is released suddenly into a chamber where the powder is located. This causes the powder to mix turbulently, which breaks up large particles and "loads" them with pressurized gas. When they are broken down small enough in size, they move through an ejecting conduit, and quickly into an exit nozzle of sudden increase in diameter. This causes the pressurized gas stored in the particles to depressurize suddenly, which breaks the pressurized agglomerates into a fine aerosol.

Figure 1:
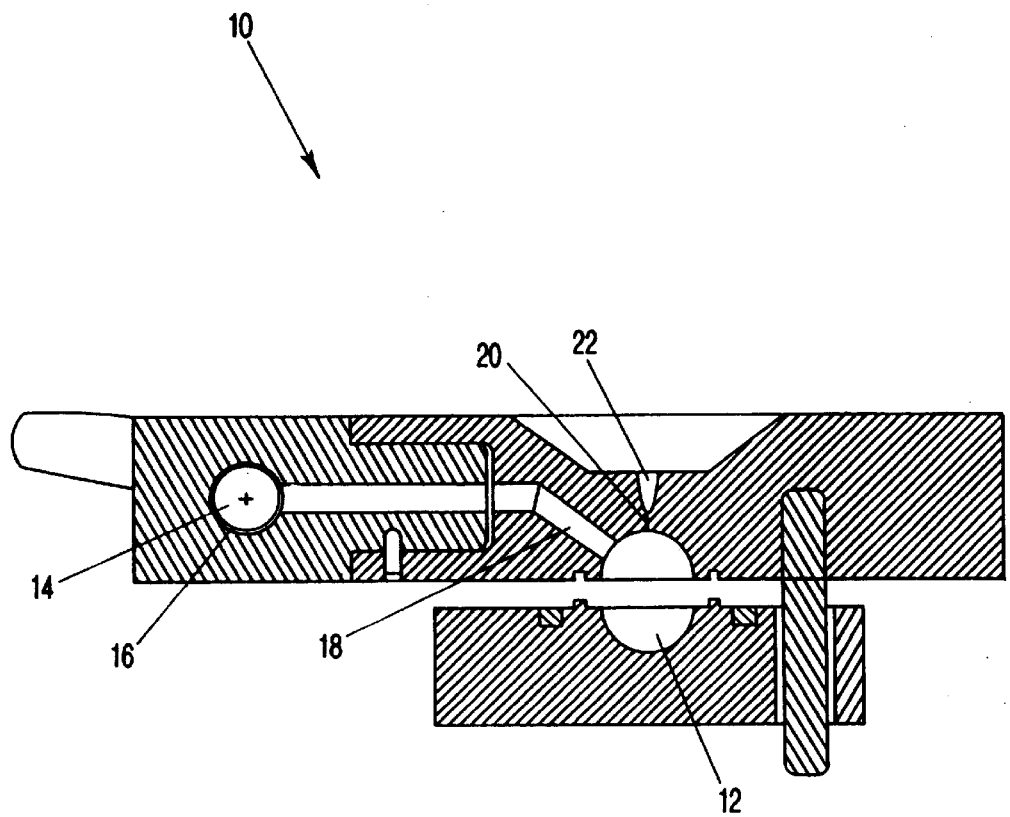
FIG. 1 is a side, cutaway view of the preferred embodiment of an aerosol generator of the present invention.

FIGS. 1–5 show the preferred embodiment of the present invention. In FIG. 1, the preferred embodiment of aerosol generator 10, powder chamber 12 is preferably spherical to minimize the wall surface area per unit volume, although other configurations (e.g. half-sphere, ovoid, cylinder) may also be used. Pressure chamber 14, fast releasing valve 16, pressure conduit 18, and ejecting conduit 20 are part of the upper section of aerosol generator 10. In this embodiment, a single pressure conduit 18 enters powder chamber 12 along a tilted polar axis of chamber 12. Alternatively, more than one pressure conduit 18 can be used. Ejecting conduit 20 begins abruptly in powder chamber 12 and ends abruptly in exit nozzle 22.

Figure 2:
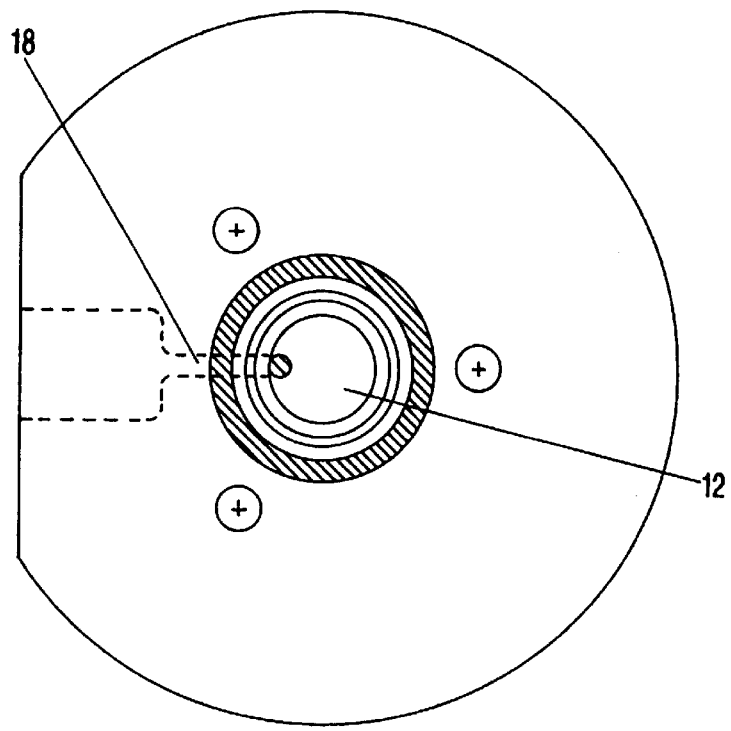
FIG. 2 is a cross-sectional top view of the powder chamber of the FIG. 1 embodiment showing arrangement with one pressure conduit.
Figure 3:
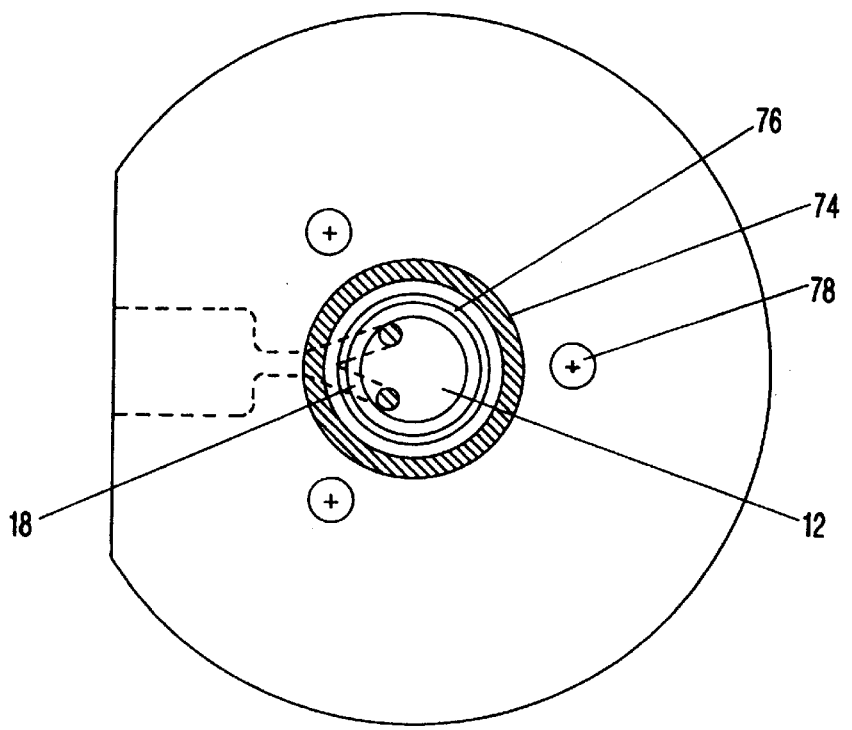
FIG. 3 is a cross-sectional top view of the powder chamber of the FIG. 1 embodiment showing arrangement with two pressure conduits.

FIGS. 2–3 show preferred placements of pressure conduits 18. Pressure conduits 18 are arranged to induce a highly turbulent, but not a rotating, flow during the pressurizing phase. A strong rotation would increase residual deposition of powder on powder chamber walls due to the strong centrifugal forces imposed on the particle agglomerates by the rotating carrier gas.

In a preferred embodiment, one pressure conduit is used. An alternative preferred embodiment of aerosol generator 10 utilizes two pressure conduits. Alternatively, three or more pressure conduits can be used.

A turbulent, non-rotating flow can be induced by the following means: FIG. 2 shows one pressure conduit 18—the gas enters the powder chamber along a polar axis through chamber 12. The flow splits symmetrically at the opposite wall. FIG. 3 shows two pressure conduits 18—conduits 18 are arranged to induce maximum turbulence by allowing injected or deflected gas streams to collide in powder chamber 12. The cross-sectional area of pressure conduit(s) 18 is optimized so as to add as little volume to the system as possible, yet create as little friction losses as possible to the pressurizing gas.

Another important variable in aerosol generator 10 is the ratio of the volumes of pressure chamber 14 to powder chamber 12. The volume of pressure chamber 14 is related to the volume of powder chamber 12 so as to provide a suitable relationship between the pressure range at which agglomerates are formed and the pressure range at which the aerosol is generated. Applying Boyles Law gives POej= PO*Vpr/(Vpr+Vpw), wherein POej is the initial pressure at which the aerosol is generated, PO is the initial pressure of the pressure chamber, Vpr is the volume of the pressure chamber, and Vpw is the volume of the powder chamber and pressure conduits. For example, at 50 atm feeding pressure and volumes of Vpr=2 and Vpw=1mL, the pressure will be 33 atm when the aerosol begins to be generated. The volume ratios of Vpr to Vpw can be from 1:1 to 10:1, depending on the driving pressure. Because the powder chamber during ejection can be regarded as a well-mixed tank, a total of at least ten powder chamber-volumes of air/gas is sufficient to extract most suspended particles from the powder chamber. Too little gas may not extract all the powder, and too much gas dilutes the ejected aerosol bolus to lower particle concentrations and pushes the aerosol cloud too far away from the aerosol generator.

Figure 4:
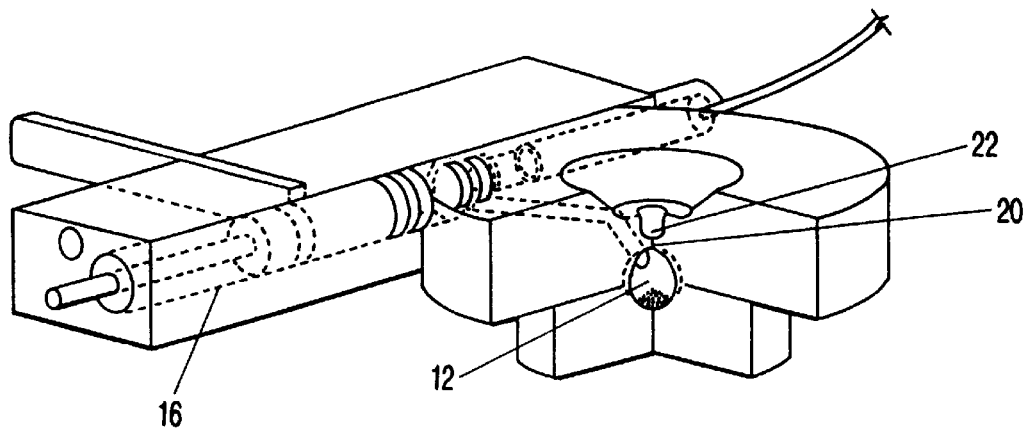
FIG. 4 is a perspective view of an aerosol generator before trigger release.
Figure 5:
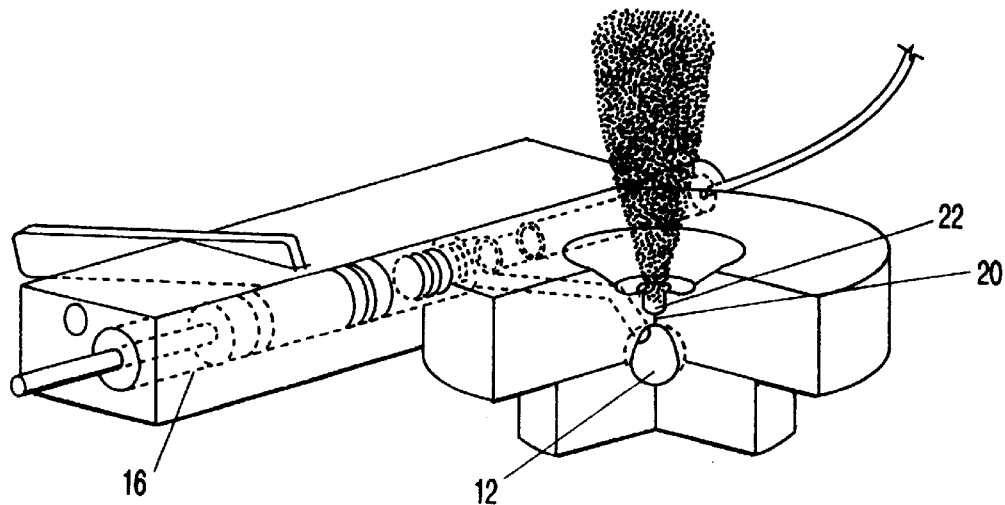
FIG. 5 is a perspective view of an aerosol generator after trigger release.

FIGS. 4–5 illustrate the two-step mechanism of aerosol generator 10. FIG. 4 shows the preferred embodiment after powder has been loaded into chamber 12, but before valve 16 release. In FIG. 5 when valve 16 is released, powder chamber 12 is pressurized under intense turbulent mixing. During this phase the powder is fractionated into agglomerates small enough to pass through ejecting conduit 20. Concurrently, the powder agglomerates are loaded with pressurized gas, which serves as the principal force behind aerosolization during the subsequent step of decompression. In the second step the suspended particle agglomerates are ejected through ejecting conduit 20. Ejecting conduit 20 has a substantially constant cross-sectional area and begins abruptly in powder chamber 12, without any tapered inlet end. It is preferably cylindrical in shape, although other cross-sectional shapes, such as square or triangular can be used as long as substantially constant throughout the cross-section of ejecting conduit 20. Ejecting conduit 20 has two functions: to constitute the overall critical orifice that regulates the ejection time of the carrier gas at the required driving pressures, and to maintain the static pressure of the aerosol dispersion as high as possible before it enters exit nozzle 22. In order to keep the static pressure high until decompression, the gas speed should be kept as low as possible. The abrupt inlet end creates an equally abrupt transfer of powder agglomerates from the highly turbulent flow field in powder chamber 12 to a very small inlet flow pattern at ejecting conduit 20. The result is a very high acceleration of particle agglomerates immediately before entering the critical orifice of ejecting conduit 20. Therefore, ejecting conduit 20 is never blocked—larger unbreakable particles settle to the bottom of powder chamber 12, while the agglomerates are ejected.

Figure 6:
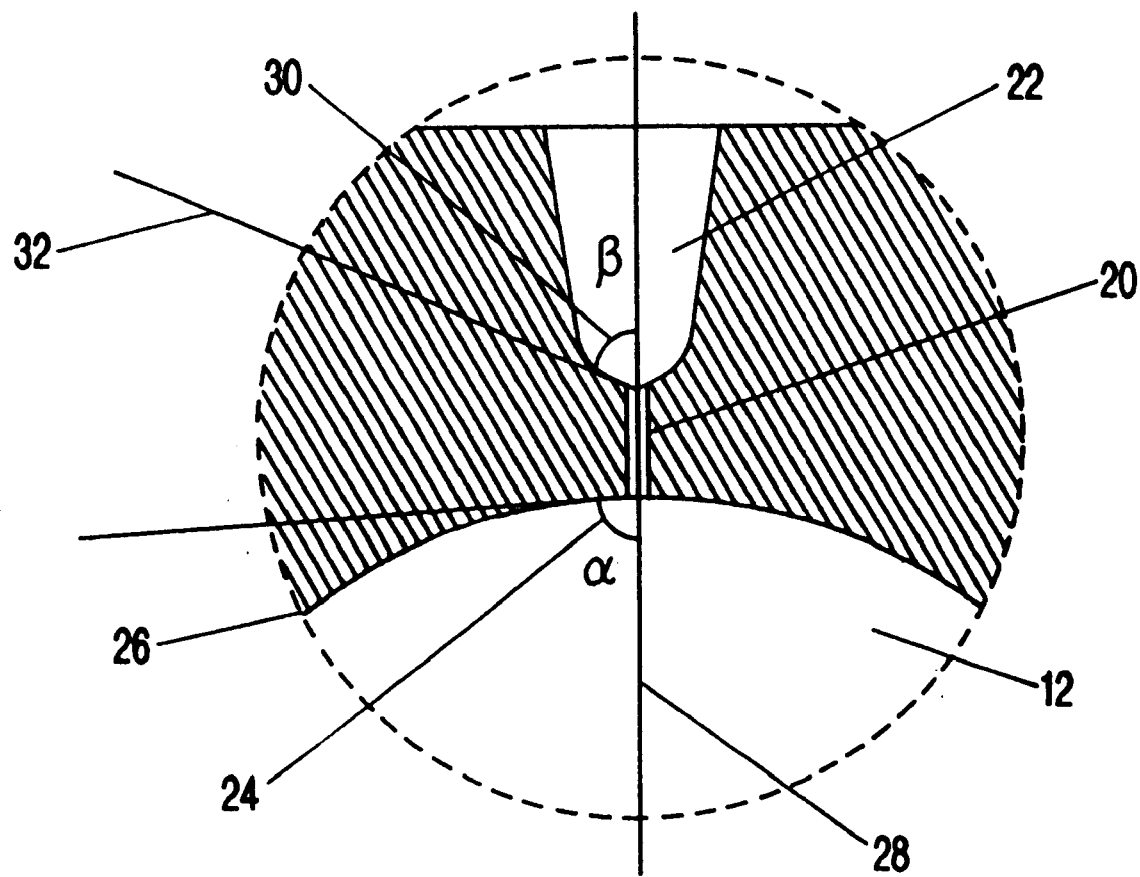
FIG. 6 is a vertical cross-section of the powder chamber lid of the preferred embodiment showing relevant angles of components.

FIG. 6 shows the angle necessary to maintain the high acceleration. Angle $\alpha$ 24 between tangent 26 of the wall of powder chamber 12 in the immediate vicinity of ejecting conduit 20 and axial extension 28 of ejecting conduit 20 should be greater than 60°, and preferably greater than 85°. The sudden widening where ejecting conduit 20 reaches exit nozzle 22 allows for the fastest possible explosive expansion of the carrier gas to ambient pressure. The carrier gas trapped within the particle agglomerates creates an isotropic outward-directed fractionating force powerful enough to generate micron-sized aerosols even of cohesive powders such as albumin, all-trans retinoic acid, carbon black or diesel soot. The higher the static pressure and faster the decompression, the higher the de-agglomerating power of generator 10. Exit nozzle 22 itself is designed to fan out the aerosol at a desired speed and plume shape. To optimize these, angle $\beta$ 30 between axial extension 28 and the plane 32 along a conical surface where exit nozzle 22 meets ejecting conduit 20 should be greater than 45°, preferably greater than 70°, and preferably greater than 90°.

The mechanism of micronization of powders utilized by this invention involves predominately divergent forces, whereas devices relying upon turbulent or mechanical shear forces for micronization have distinctive convergent force components likely to cause some reagglomeration. Because decompression in the present device occurs only in a minute fraction of the gas volume at any particular moment, the high-energy output is perceived only as distinctive hissing sound. Typically, the volume of the exit conduit, where decompression occurs, is only on the order of $1/10,000^{th}$ of the volume of the powder chamber. The smaller this ratio, the gentler the aerosol formation is in terms of noise and downstream speed of aerosol plume. This ratio is much smaller than in existing devices.

Figure 7:
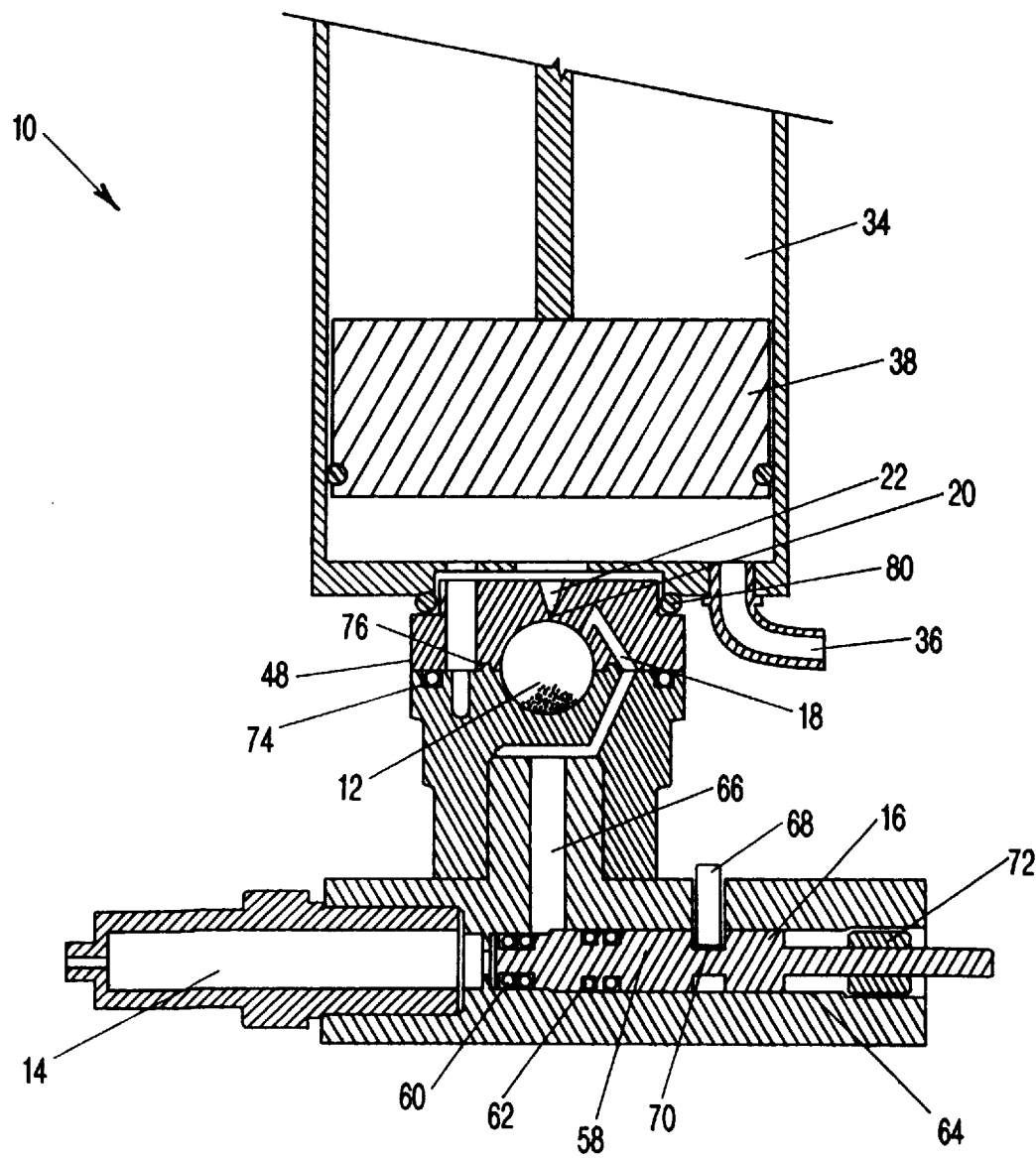
FIG. 7 is a side cutaway view of an alternative embodiment of an aerosol generator of the present invention.

FIG. 7 shows an alternative preferred embodiment of aerosol generator 10. Pressurized gas, preferably in the range of 5–100 atm, is preloaded into pressure chamber 14, which is sealed with fast-releasing valve 16. Preferably three symmetrical pressure conduits 18 transfer the pressurized gas to powder chamber 12. Alternatively, one or two pressure conduits can be used. Powder chamber 12 is divided preferably along the equatorial plane (although it can be divided above or below this), and powder is loaded. The powder ejects through a cylindrical ejection conduit 20. (Alternatively, ejection conduits 20 of other cross-sectional shapes, such as square or triangular, can be used, as long as substantially uniform in cross-section.) When used for involuntary exposures in laboratory animals, a syringe 34 is mounted on top of aerosol generator 10. When generator 10 is triggered aerosol outlet 36 is closed, and the generated bolus pushes up plunger 38. Immediately after plunger 38 has reached its top position, aerosol outlet 36 is opened and the aerosol can be ejected from syringe 34.

Figure 8:
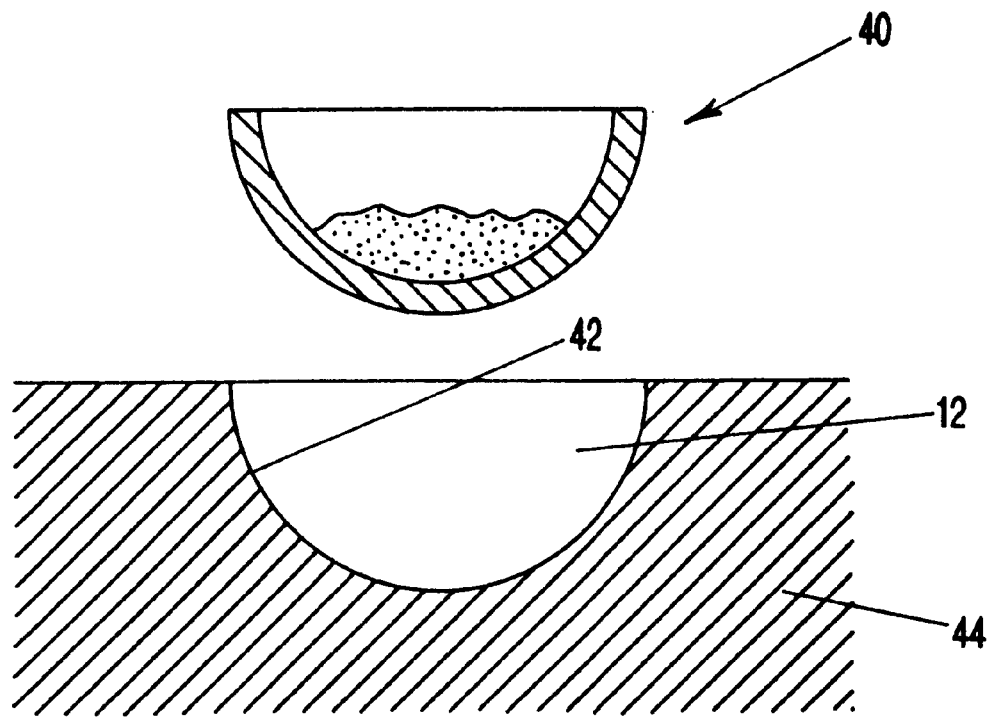
FIG. 8 is the cutaway side view of the preferred powder supply receptacle.

FIGS. 8–11 illustrate alternative embodiments for powder supply. FIG. 8 shows one such embodiment. In FIG. 8, powders are prepackaged into sealed cups 40 (preferably hemispheric shaped cups) that fit snugly within indentation 42 of base 44 of powder chamber 12. These can be inserted one at a time, or supplied on a cartridge containing multiple cups for repeated dosing.

Figure 9:
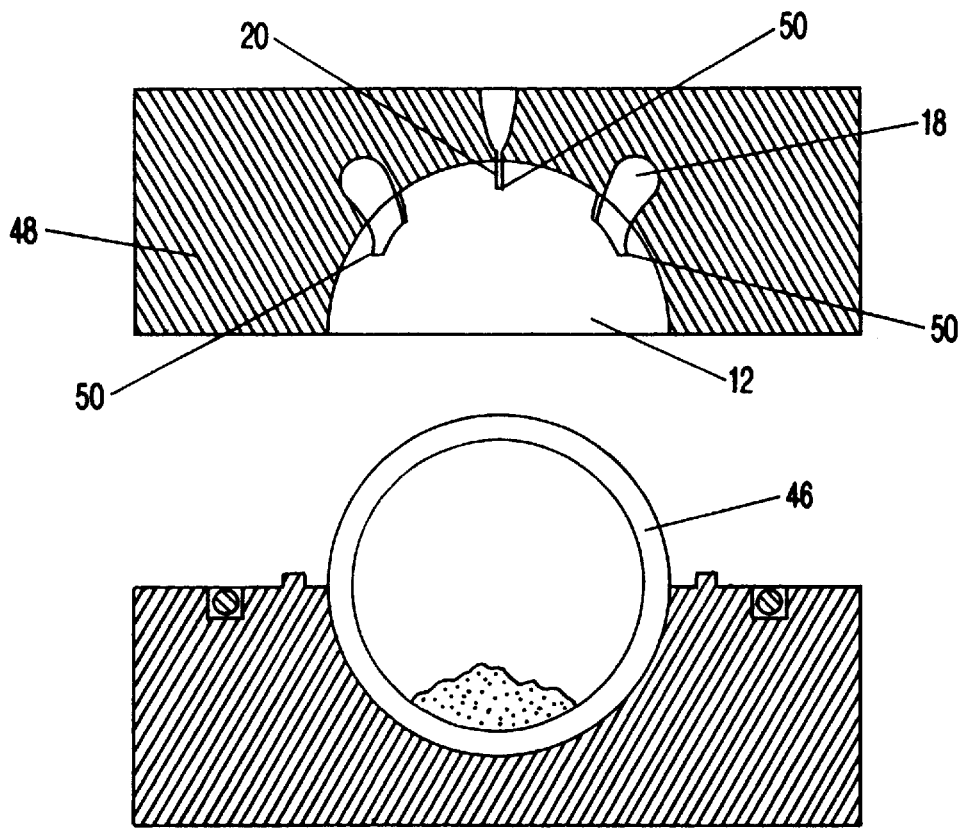
FIG. 9 is a cutaway side view of an alternative powder supply receptacle prior to loading.
Figure 10:
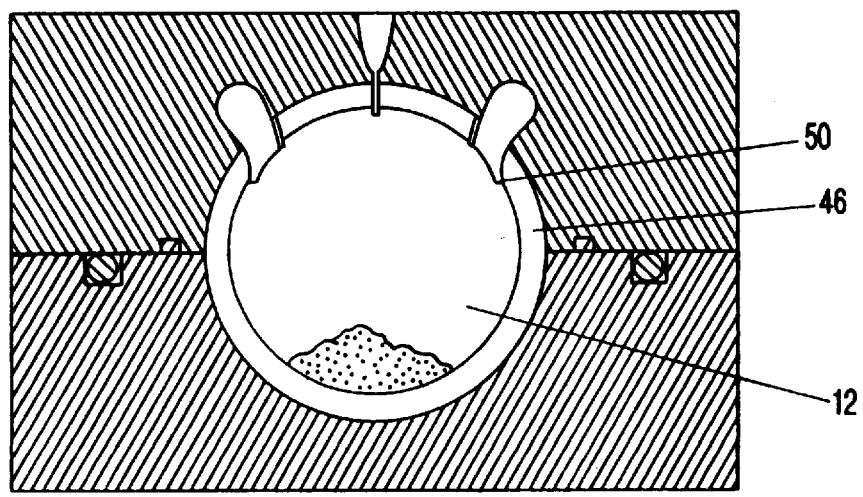
FIG. 10 is a cutaway side view of an alternative powder supply receptacle of FIG. 9 during use of the present invention.

In FIGS. 9 and 10, powder medicaments are supplied in airtight capsules (preferably spheres) 46, which fit snugly inside powder chamber 12. Rotational orientation is thus irrelevant. FIG. 9 illustrates lid 48 of powder chamber 12 with piercing mechanisms 50 located on the ends of ejecting conduit 20 and pressure conduits 18. Piercing mechanisms 50 pierce through the surface of sphere 46 when lid 48 is lowered, as shown in FIG. 10. This results in much less contamination of interior surfaces of aerosol generator 10.

Figure 11:
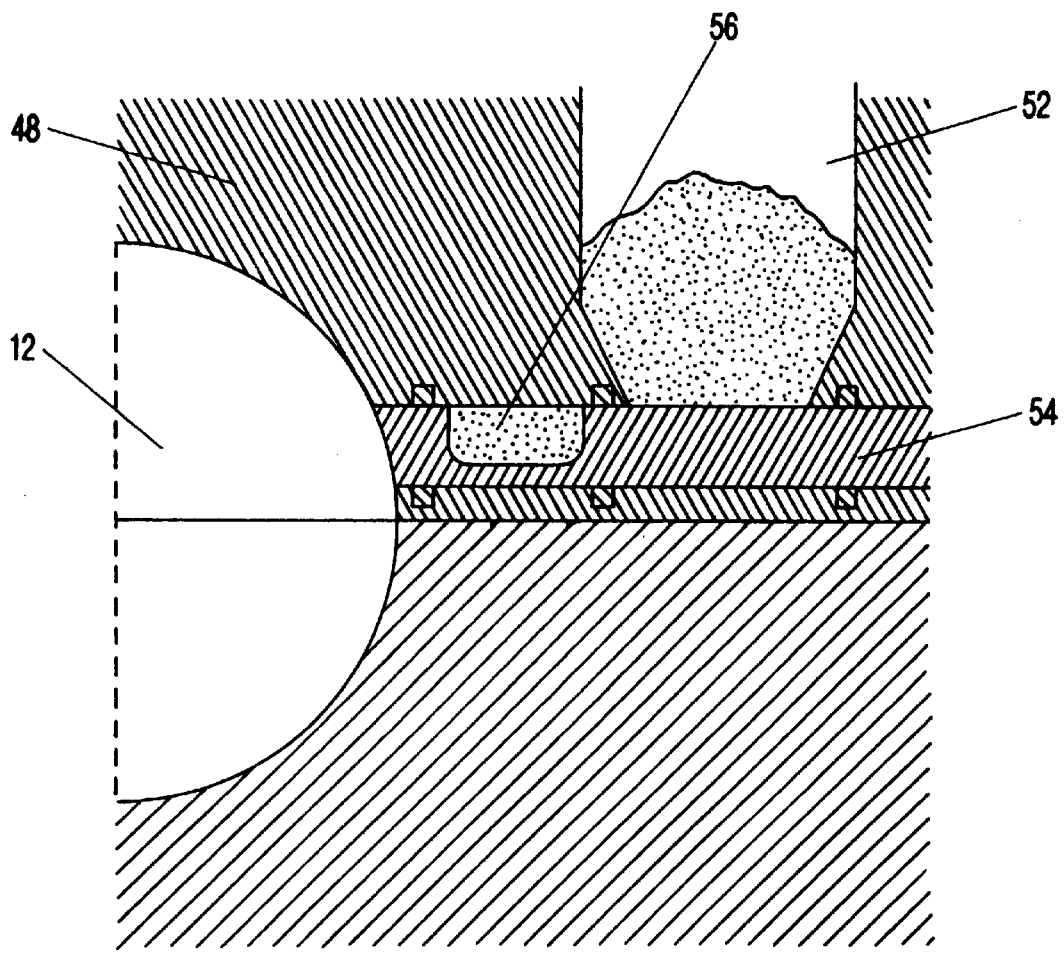
FIG. 11 is a cutaway side view of an alternative powder supply consisting of a reservoir.

FIG. 11 shows another embodiment of powder supply. Powder is transferred from reservoir 52 located in lid 48 next to powder chamber 12. The powder is transferred by means of dowel 54 that stretches from reservoir 52. The end of dowel 54 completes the spherical shape of powder chamber 12 in its non-dosing position. Dowel 54 has cup 56 that fills with powder when dowel 54 is first pulled back under reservoir 52. It is then pushed forward into powder chamber 12, where dowel 54 is rotated, thus turning cup 56 over and emptying its contents into powder chamber 12. Dowel 54 is then pulled back to seal powder chamber 12.

In addition, there are several peripheral components, as illustrated in the alternative preferred embodiment in FIG. 7. Pressure chamber 14 is sealed with fast-releasing valve 16 preferably comprising rod 58 of circular cross-section with two sets of O-rings 60, 62 sealing against shaft 64 upstream and downstream of conduit 66 leading to powder chamber 12. Upstream O-rings 60 are slightly smaller than downstream O-rings 62 to prevent damage when rod 58 is released. Other sealing mechanisms (e.g. plastic gaskets) can be used. Rod 58 is released when trigger 68 settled in notch 70 is depressed raising triger 68 out of notch 70 and rod 58 is pushed by the gas pressure to stop against stopper 72. A spring around rod 58 may be included to be compressed against stopper 72 when valve 16 is released, and decompressed to push rod 58 back into a cocked position when the pressure has dropped within pressure chamber 14. This provides a means to reduce the volume of the air/gas to be ejected with the aerosol bolus while maintaining initial driving pressure.

Seals are also preferably included in aerosol generator 10 at other locations. For example, in FIG. 7, lid 48 of powder chamber 12 is sealed both with O-ring 74 and with circular square-profile ridge 76, and closed with three bolts 78. (See also FIG. 3) Other types of seals (e.g. plastic gaskets) can be used alone or in combination, or alternatively powder chamber 12 can be fitted without supplemental seals. Also, syringe 34 in FIG. 7 is sealed against lid 48 of aerosol generator 10 with O-ring 80.

The following non-limiting examples illustrate effectiveness of two preferred embodiments of the invention.

EXAMPLE 1

In the first experiment, bottled nitrogen of pressures up to 100 atm served as the pressure source. Powders were weighed on a Cahn microbalance (Model 31, Cahn Instruments, Cerritos, Calif.). Particle size distribution was measured with a quartz crystal microbalance cascade impactor (California Measurements Inc.). A steel syringe of 250 mL volume was mounted directly on top of the aerosol generator. With the aerosol exit from the syringe closed, a vacuum was applied to the syringe with the plunger fixed at a 100 mL volume. This procedure reduced the amount of particles depositing on the plunger. Different amounts of particulates were loaded to the device, and the pressure chamber was brought up to the desired driving pressure. Immediately after the generator was triggered, and the plunger of the syringe was elevated to its full volume, the aerosol bolus was pushed into a 25 mm glass fiber filter (Gelman Series, Ann Arbor, Mich.). Amounts of particles on the filter were determined by rinsing the equipment in a known volume of ethanol, then comparing the light extinction in a spectrophotometer (Perkins Elmer Lambda 6 UV/VIS) with known standard curves for the same powders. The fraction calculated to be retained in the syringe was assumed to complete the mass balance between the amount loaded into the powder chamber, and the amount collected on the filter plus the amount retained in the powder chamber.

Results showed that, with diesel soot and carbon black, the 1 mL generator ejected from 25% to 65% of the loaded amounts of dust when the amount loaded was increased from 0.05 to 0.5 mg. Over the same range of particle amounts the fraction collected from the exposure syringe on filter paper increased from 6% to 15%. When the dusts were ejected at 90 atm driving pressure, the mean mass aerodynamic diameter (MMAD) was in the range of 0.2–4 $\mu$m, with a range of 1–3 $\mu$m. The generator can aerosolize amounts of powder of up to at least 5 mg.

EXAMPLE 2

The second embodiment consisted of a 0.3 mL powder chamber, where the pressurizing gas was conducted directly from the pressure chamber into the powder chamber along a polar axis in a single conduit. The generator ejected the aerosol directly into a fixed volume holding chamber of 400 mL volume. The aerosol ejected into the holding chamber was sampled directly into the quartz crystal microbalance cascade impactor for determining the particle size distribution. Depending on the properties of the aerosolized particles, the device generated micron-sized aerosols using driving pressures ranging from 20–100 atm. Carbon black and diesel soot, porous yet highly adhesive dusts, were aerosolized to 2–5 $\mu$m with only 20–30 atm driving pressure. With pure albumin (SIGMA A-7888), an aerosol with a MMAD of 1.9–±0.2 $\mu$m was generated by the device at 80 atm driving pressure in loaded amounts of up to 1.0 mg, and the same amounts of all-trans retinoic acid (Aldrich Chemical company 22,301-8) were fractionated into particles around 2–3 micrometer MMAD over a wide range of driving pressures.

The preceding examples can be repeated with similar success by substituting the generically or specifically described reactants and/or operating conditions of this invention for those used in the preceding examples. They showed the effectiveness of using the invention to aerosolize adhesive powders, and demonstrated the lack of clogging from repeated use.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for aerosolizing and dispensing powders, said apparatus comprising:

a pressure chamber;

at least one substantially straight ejecting conduit opening at an exit nozzle to ambient pressures;

an enclosed powder chamber for loading with a pressurized gas and mixing the powder; and at least one pressure conduit connecting said pressure chamber and said powder chamber.

2. The apparatus of claim 1 wherein said ejecting conduit comprises a channel of substantially uniform cross-section.

3. The apparatus of claim 2 wherein said ejecting conduit comprises a cylinder.

4. The apparatus of claim 1 wherein said powder chamber further comprises a base comprising an indentation for receiving powder.

5. The apparatus of claim 4 wherein said powder chamber further comprises a lid.

6. The apparatus of claim 5 wherein said lid further comprises an indentation.

7. The apparatus of claim 6 wherein said lid indentation is disposed over said base indentation.

8. The apparatus of claim 1 wherein said powder chamber comprises a sphere.

9. The apparatus of claim 1 wherein said exit nozzle and said ejecting conduit meet at an angle at least 45 degrees from an axial extension of said ejecting conduit and a plane of said exit nozzle.

10. The apparatus of claim 9 wherein said angle is at least 70 degrees.

11. The apparatus of claim 10 wherein said angle is at least 90 degrees.

12. The apparatus of claim 1 wherein said powder chamber and said ejecting conduit meet at an angle greater than 60 degrees from an axial extension from said ejecting conduit and a tangent of said powder chamber.

13. The apparatus of claim 12 wherein said angle is greater than 85 degrees.

14. The apparatus of claim 1 further comprising a fast-releasing valve for releasing a pressurized gas and activating said apparatus.

15. The apparatus of claim 1 further comprising a reservoir for holding powders and a line connecting said reservoir and said powder chamber.

16. The apparatus of claim 1 further comprising a pressurized gas supply.

17. The apparatus of claim 16 wherein said gas supply comprises at least one gas selected from the group consisting of nitrogen, air and the inert gases.

18. An apparatus for aerosolizing and dispensing powders, said apparatus comprising:

a pressure chamber;

an enclosed powder chamber for loading with a pressurized gas and mixing the powder;

at least one pressure conduit connecting said pressure chamber and said powder chamber; and at least one substantially straight ejecting conduit of substantially uniform cross-section opening at an exit nozzle.

19. The apparatus of claim 18 wherein said ejecting conduit comprises a cylinder.

20. The apparatus of claim 18 wherein said powder chamber further comprises a base comprising an indentation for receiving powder.

21. The apparatus of claim 20 wherein said powder chamber further comprises a lid.

22. The apparatus of claim 21 wherein said lid further comprises an indentation.

23. The apparatus of claim 22 wherein said lid indentation is disposed over said base indentation.

24. The apparatus of claim 18 wherein said powder chamber comprises a sphere.

25. The apparatus of claim 18 wherein said exit nozzle and said ejecting conduit meet at an angle at least 45 degrees from an axial extension of said ejecting conduit and a plane of said exit nozzle.

26. The apparatus of claim 25 wherein said angle is at least 70 degrees.

27. The apparatus of claim 25 wherein said angle is at least 90 degrees.

28. The apparatus of claim 18 wherein said powder chamber and said ejecting conduit meet at an angle greater than 60 degrees from an axial extension from said ejecting conduit and a tangent of said powder chamber.

29. The apparatus of claim 28 wherein said angle is greater than 85 degrees.

30. The apparatus of claim 18 further comprising a fast-releasing valve for releasing a pressurized gas and activating said apparatus.

31. The apparatus of claim 18 further comprising a pressurized gas supply.

32. An apparatus for aerosolizing and dispensing powders, said apparatus comprising:

a pressure chamber;

at least one substantially straight ejecting conduit;

an enclosed powder chamber for loading with a pressurized gas and mixing the powder, said powder chamber and said ejecting conduit meeting at an angle greater than 60 degrees from an axial extension from said ejecting conduit and a tangent of said powder chamber; and at least one pressure conduit connecting said powder chamber and said pressure chamber.

33. The apparatus of claim 32 wherein said angle is greater than 85 degrees.

34. The apparatus of claim 32 wherein said ejecting conduit comprises a channel of substantially uniform cross-section.

35. The apparatus of claim 34 wherein said ejecting conduit comprises a cylinder.

36. The apparatus of claim 32 wherein said powder chamber further comprises a base comprising an indentation for receiving powder.

37. The apparatus of claim 36 wherein said powder chamber further comprises a lid.

38. The apparatus of claim 37 wherein said lid further comprises an indentation.

39. The apparatus of claim 38 wherein said lid indentation is disposed over said base indentation.

40. The apparatus of claim 32 wherein said powder chamber comprises a sphere.

41. The apparatus of claim 32 wherein said exit nozzle and said ejecting conduit meet at an angle at least 45 degrees from an axial extension of said ejecting conduit and a plane of said exit nozzle.

42. The apparatus of claim 41 wherein said angle from an axial extension of said ejecting conduit and a plane of said exit nozzle is at least 70 degrees.

43. The apparatus of claim 41 wherein said angle from an axial extension of said ejecting conduit and a plane of said exit nozzle is at least 90 degrees.

44. The apparatus of claim 32 further comprising a fast-releasing valve for releasing a pressurized gas and activating said apparatus.

45. The apparatus of claim 32 further comprising a pressurized gas supply.

46. An apparatus for aerosolizing and dispensing powders, said apparatus comprising:
   a pressure chamber;
   at least one substantially straight ejecting conduit, of substantially uniform cross-section opening at an exit nozzle;
   an enclosed powder chamber for loading with a pressurized gas and mixing the powder; and
   at least one pressure conduit connecting said powder chamber and said pressure chamber;
   said exit nozzle and said ejecting conduit meeting at an angle at least 45 degrees from an axial extension of said ejecting conduit and a plane of said exit nozzle.

47. The apparatus of claim 46 wherein said angle is at least 70°.

48. The apparatus of claim 47 wherein said angle is at least 90 degrees.

49. The apparatus of claim 46, said ejecting conduit comprising a channel of substantially uniform cross-section.

50. The apparatus of claim 49 wherein said ejecting conduit comprises a cylinder.

51. The apparatus of claim 46 wherein said powder chamber further comprises a base comprising an indentation for receiving powder.

52. The apparatus of claim 51 wherein said powder chamber further comprises a lid.

53. The apparatus of claim 52 wherein said lid further comprises an indentation.

54. The apparatus of claim 53 wherein said lid indentation is disposed over said base indentation.

55. The apparatus of claim 46 wherein said powder chamber comprises a sphere.

56. The apparatus of claim 46 wherein said powder chamber and said ejecting conduit meet at an angle greater than 60 degrees from an axial extension from said ejecting conduit and a tangent of said powder chamber.

57. The apparatus of claim 56 wherein said angle from an axial extension from said ejecting conduit and a tangent of said powder chamber is greater than 85 degrees.

58. The apparatus of claim 46 further comprising a fast-releasing valve for releasing a pressurized gas and activating said apparatus.

59. The apparatus of claim 46 further comprising a pressurized gas supply.

60. A method of generating a fine aerosol from a powder substance comprising the following steps:
   a) agitating and loading with a pressurized gas a powder in an enclosed powder chamber to create a pressurized suspension;
   b) ejecting the suspension through a narrow substantially straight ejecting conduit of substantially uniform cross-section;
   c) passing the pressurized suspension from the narrow ejecting conduit directly into an exit nozzle of sudden diameter increase into ambient pressure; and
   d) depressurizing the suspension to de-agglomerate the suspension.

61. The method of claim 60 further comprising the step of administering the suspension to a patient's lung.

62. The method of claim 61 wherein the suspension reaches alveoli and peripheral lung.

63. The method of claim 60 wherein the substance administered comprises at least one substance selected from the group consisting of peptides, genes, vitamins, polymers, and medicaments.

64. The method of claim 60 wherein the step of ejecting the suspension through a narrow ejecting conduit comprises ejecting the suspension from the powder chamber wherein the powder chamber and the ejecting conduit meet at an angle greater than 60 degrees from an axial extension from the ejecting conduit and a tangent of the powder chamber.

65. The method of claim 64 wherein the angle is greater than 85 degrees.

66. The method of claim 60 wherein the step of passing the suspension from the narrow conduit directly into an exit nozzle comprises passing the suspension from the ejecting conduit wherein the exit nozzle and the ejecting conduit meet at an angle of at least 45 degrees from an axial extension of the ejecting conduit and a plane of the exit nozzle.

67. The method of claim 66 wherein the angle is at least 70 degrees.

68. The method of claim 66 wherein the angle is at least 90 degrees.

69. A method of generating a fine aerosol from an agglomerated powder wherein clogging of an aerosol generator is avoided comprising the following steps:
   a) agitating and loading with a pressurized gas an agglomerated powder to create a pressurized suspension in the aerosol generator;
   b) ejecting the suspension through a narrow ejecting conduit in the aerosol generator;
   c) passing the pressurized suspension from the narrow conduit directly into an exit nozzle of sudden diameter increase into ambient pressure; and
   d) depressurizing the suspension to de-agglomerate the suspension.

70. The method of claim 69 further comprising the step of administering the suspension to a patient's lung.

71. The method of claim 70 wherein the suspension reaches alveoli and peripheral lung.

72. The method of claim 71 wherein the suspension administered comprises at least one substance selected from the group consisting of peptides, genes, vitamins, polymers, and medicaments.

73. The method of claim 69 wherein the step of ejecting the suspension through a narrow ejecting conduit comprises ejecting the suspension through a channel of substantially uniform cross-section.

74. The method of claim 73 wherein the ejecting conduit is a cylinder.

75. A method of generating a fine aerosol from a powder substance comprising the following steps:
   a) agitating and loading with a pressurized gas a powder substance to create a pressurized suspension;

b) ejecting the suspension through a narrow ejecting conduit of substantially uniform cross-section;

c) passing the pressurized suspension from the narrow conduit directly into an exit nozzle of sudden diameter increase into ambient pressure; and d) depressurizing the suspension to de-agglomerate the suspension.

76. The method of claim 75 further comprising the step of administering the suspension to a patient's lung.

77. The method of claim 75 wherein the step of ejecting the suspension through a narrow ejecting conduit comprises ejecting the suspension through a cylinder.

78. The method of claim 75 wherein the suspension administered comprises at least one substance selected from the group consisting of peptides, genes, vitamins, polymers, and medicaments.

* * * * *